| United States Patent [19]
Tamaru et al.

[11] Patent Number: 4,877,900
[45] Date of Patent: Oct. 31, 1989

[54] PROCESS FOR PREPARING TEREPHTHALIC ACID OF HIGH QUALITY

[75] Inventors: Akio Tamaru; Yoshiaki Izumisawa, both of Kitakyushu, Japan

[73] Assignee: Mitsubishi Chemical Industries Limited, Tokyo, Japan

[21] Appl. No.: 177,951

[22] Filed: Apr. 5, 1988

[30] Foreign Application Priority Data

Apr. 24, 1987 [JP] Japan .............................. 62-101373

[51] Int. Cl.$^4$ ........................................... C07C 51/265
[52] U.S. Cl. .................................... 562/413; 562/412; 562/416; 562/486; 562/487
[58] Field of Search ............... 562/412, 416, 486, 487, 562/413

[56] References Cited

U.S. PATENT DOCUMENTS 4,447,646  5/1984  Johnson et al. ...................... 562/487
4,605,763  8/1986  Kiefer et al. ......................... 562/487

*Primary Examiner*—Werren B. Lone
*Assistant Examiner*—Vera C. Clarke
*Attorney, Agent, or Firm*—Oblon, Spivak, McClelland, Maier & Neustadt

[57] ABSTRACT

The present invention provides a process of preparing terephthalic acid of high quality which is characterized by:

oxidizing p-xylene with molecular oxygen in an acetic acid solvent in the presence of a catalyst comprised of at least one heavy metal and bromine at a temperature of from 180° to 230° C. to convert at least 95 wt % of the p-xylene into terephthalic acid and, optionally, subjecting the resultant reaction mixture to low temperature post-oxidation with molecular oxygen at temperatures lower than the temperature of the first oxidation reaction, thereby obtaining a slurry containing terephthalic acid particles whose spectral reflectance defined below is not less than 70% and whose reflectance ratio (400/500) defined below is not less than 0.92;

subjecting the slurry to high temperature post-oxidation with molecular oxygen at a temperature of from 235° to 290° C. and then to crystallization; and collecting the resultant terephthalic acid from the reaction mixture.

Spectral reflectance = a spectral reflectance at 500 nm determined according to a white light illumination method.

Reflectance ratio (400/500) = (spectral reflectance at 400 nm)/(spectral reflectance at 500 nm).

19 Claims, 3 Drawing Sheets

PROCESS FOR PREPARING TEREPHTHALIC ACID OF HIGH QUALITY

FIELD OF THE INVENTION

This invention relates to a process for the preparation of terephthalic acid of high quality and more particularly, to a process for the preparation of high-quality terephthalic acid which can yield polyesters having good whiteness by direct reaction with glycols.

DISCUSSION OF BACKGROUND

In recent years, for the preparation of polyesters such as polyethylene-terephthalate or polybutyleneterephthalate, it is the general practice to use a process of directly reacting terephthalic acid with glycols without using dimethyl-terephthalate as a starting material. This process is called a direct polymerization process. In this process, the terephthalic acid used as the starting material should have a quality as high as possible.

Terephthalic acid used for the direct polymerization has been prepared by a process in which crude terephthalic acid crystals obtained by air oxidation of a p-xylene in liquid phase have been once separated for collection, after which they are dissolved in a water solvent under high temperature and high pressure conditions and purified by hydrogenation in the presence of a palladium-carbon catalyst. However, the purified terephthalic acid obtained by the above process contains a small amount of impurities which emit fluorescence at a wavelength of 420 to 480 nm. Accordingly, the terephthalic acid was rather unsuitable as a starting material for the preparation of polyesters because color rendering (i.e. a tendency to produce a hue difference according to a light source) is one of problems to solve.

On the other hand, another process is known in which a slurry containing terephthalic acid crystals obtained by air oxidation of p-xylene in liquid-phase is subsequently subjected to post-oxidation under certain conditions to obtain terephthalic acid usable as the direct polymerization. (Japanese Patent Publication No. 47864/1987) This process is not only advantageous in that high-quality terephthalic acid is obtained in one plant, but also advantageous in that the terephthalic acid contains a reduced amount of fluorescent impurities.

However, the quality of terephthalic acid is generally expressed by alkali transmission wherein the wavelength is approximately from 340 to 400 nm from the standpoint of the sensitivity of measurement. With the above terephthalic acid, even though the alkali transmission is good, the whiteness of a polymer obtained from the terephthalic acid is not necessarily satisfactory.

Under these circumstances in the art, the present inventors have made extensive studies of a process of preparing terephthalic acid useful in the direct polymerization, in which a slurry containing terephthalic acid produced by air oxidation of p-xylene in liquid phase is subjected to post-oxidation, so as to obtain terephthalic acid of high quality. When the terephthalic acid is used to prepare polyesters, the resultant polymer has an improved degree of whiteness. As a result, it has been found that the quality of terephthalic acid should not be evaluated by alkali transmission, but should be assessed by spectral reflectance at 400 to 500 nm in order to permit a closer relation to the whiteness of a polymer obtained from the terephthalic acid. Based on the above finding, the present inventors have made further studies on the preparation of high-quality terephthalic acid. As a result, it has also been found that in order to obtain high-quality terephthalic acid useful in preparing polyesters whose whiteness is good, the spectral reflectance of terephthalic acid crystals in a slurry prior to the post-oxidation should be controlled to be within a certain range. The present invention is accomplished based on the above findings.

SUMMARY OF THE INVENTION

The present invention provides a process of preparing terephthalic acid of high quality which is characterized by:

oxidizing p-xylene with molecular oxygen in an acetic acid solvent in the presence of a catalyst comprised of at least one heavy metal and bromine at a temperature of from 180° to 230° C. to convert at least 95 wt % of the p-xylene into terephthalic acid and, optionally, subjecting the resultant reaction mixture to low temperature post-oxidation with molecular oxygen at temperatures lower than the temperature of the first oxidation reaction, thereby obtaining a slurry containing terephthalic acid particles whose spectral reflectance defined below is not less than 70% and whose reflectance ratio (400/500) defined below is not less than 0.92;

subjecting the slurry to high temperature post-oxidation with molecular oxygen at a temperature of from 235° to 290° C. and then to crystallization; and collecting the resultant terephthalic acid from the reaction mixture.

Spectral reflectance = a spectral reflectance at 500 nm determined according to a white light illumination method.

Reflectance ratio (400/500) = spectral reflectance at 400 nm)/(spectral reflectance at 500 nm).

DETAILED DESCRIPTION OF THE PREFERRED EMBODIMENTS

The present invention is described in more detail.

The process of preparing terephthalic acid to which the present invention is directed is broadly a process in which p-xylene is reacted with molecular oxygen in an acetic acid solvent in the presence of at least one heavy metal and bromine.

In the practice of the invention, not less than 95 wt %, preferably not less than 98 wt % of starting p-xylene is usually oxidized into terephthalic acid in a first reactor of an agitated vessel type having a condenser at an upper portion thereof. The reaction temperature is generally from 180° to 230° C., preferably from 190° to 210° C., and the pressure is from several kg/cm$^2$ to 100 kg/cm$^2$, preferably from 10 to 30 kg/cm$^2$. If the reaction temperature is too low, p-xylene cannot be oxidized satisfactorily. On the contrary, when the temperature is too high, not only terephthalic acid of high quality cannot be obtained, but also a combustion loss of the acetic acid solvent unfavorably increases. The reaction time in the first reactor should be sufficient for oxidation of not less than 95 wt % of p-xylene into terephthalic acid. The time is generally from 30 to 200 minutes, preferably from 40 to 150 minutes. In the oxidation reaction, a substantial amount of terephthalic acid is usually produced as crystals.

The catalyst used in the practice of the invention generally contains three elements of cobalt, manganese and bromine. For this purpose, a cobalt compound is usually used in an amount of from 120 to 600 ppm, preferably from 150 to 400 ppm, calculated as cobalt metal based on the solvent used, and a manganese compound is preferably used in an amount of 0.3 to 1.5 times, as manganese metal, the amount of the cobalt. A bromine compound is usually used in an amount of from 500 to 2000 ppm, preferably from 600 to 1400 ppm, as bromine, based on the solvent. Examples of the compounds include cobalt compounds such as cobalt acetate, cobalt naphthenate and the like, manganese compounds such as manganese acetate, manganese naphthenate and the like, and bromine compounds such as hydrogen bromide, sodium bromide, cobalt bromide, manganese bromide and the like, when manganese bromide and/or cobalt bromide is used, it serves as two catalytic components.

The ratio by weight between p-xylene and the solvent supplied to the first reactor is generally 1:2 to 1:6. If the solvent is too small in amount, the agitation in the reactor does not proceed satisfactorily. The use of the solvent in too small an amount is also disadvantageous in that the high temperature post-oxidation described hereinafter doe not proceed in a satisfactory manner. The acetic acid solvent may contain water in amounts of, for example, not larger than 20 wt %. The molecular oxygen passed through the liquid phase of the first reaction zone is usually in the form of air and is fed in an amount of from 3 to 100 moles per mole of the p-xylene. In general, the molecular oxygen is supplied in such a way that a concentration of oxygen in an oxidation reactor off-gas ranges from 1.5 to 8.0% by volume.

In the first oxidation reaction, the water content in the reactor may be controlled, for example, at a level of from 5 to 15 wt % by cooling a condensable gas from the reactor and removing a part of the condensate to outside without recycling it into the reactor.

The terephthalic acid-containing slurry obtained in the first reactor is subsequently subjected to high temperature post-oxidation. If necessary, it is preferred to subject, prior to the high temperature post-oxidation, the slurry to preliminary low temperature post-oxidation with molecular oxygen without further feed of p-xylene at a temperature lower by 0° to 50° C., preferably 2° to 30° C., than the reaction temperature of the first reactor, thereby effectively obtaining terephthalic acid of higher purity. In the preliminary low temperature post-oxidation, an oxidation intermediate in the mother liquor of the reaction system is mainly post-oxidized. If the treating temperature is too low, the oxidation intermediate cannot be further oxidized to a satisfactory extent. This post-oxidation time is generally in the range of from 5 to 90 minutes, preferably from 10 to 60 minutes. The amount of the molecular oxygen used in the low temperature oxidation is 1/10 to 1/1000 of the amount of molecular oxygen fed to the first reactor since products to be oxidized in the reaction mixture are small in amount. Preferably, the molecular oxygen is used in such an amount that a concentration of oxygen in the oxidation off-gas is in the range of from 1 to 8% by volume. The molecular oxygen used for this purpose may be air with or without being diluted with an inert gas.

In the practice of the invention, the slurry obtained by the above procedure is subjected to high temperature post-oxidation to obtain terephthalic acid of high quality. The present invention is characterized in that the quality of the terephthalic acid is evaluated on the basis of the spectral reflectance and the reflectance ratio defined below. The spectral reflectance of finally collected terephthalic acid is not less than 70%, preferably not less than 80%, and the reflectance ratio (400/500) is not less than 0.96, preferably from 0.965 to 1.005. Moreover, the reflectance ratio (450/500) between a reflectance at 450 nm and a reflectance at 500 nm is preferably not less than 0.985, more preferably from 0.99 to 1.005. When the spectral reflectance and the reflectance ratio satisfy the above ranges, respectively, polyesters obtained from the terephthalic acid have invariably a good degree of whiteness.

Spectral reflectance=spectral reflectance at a wavelength of 500 nm determined according a white light illumination method.

Reflectance ratio=(spectral reflectance at a wavelength of 400 nm or 450 nm)/(spectral reflectance at a wavelength of 500 nm).

For the preparation of such high-quality terephthalic acid as described above, it is necessary that terephthalic acid crystals in the slurry to be subjected to high temperature post-oxidation have a spectral reflectance of not less than 70%, preferably not less than 80%, and a reflectance ratio (400/500) of not less than 0.92, preferably from 0.93 to 0.98. Moreover, it is preferred that the reflectance ratio (450/500) between a reflectance at a wavelength of 450 and a reflectance at a wavelength of 500 is not less than 0.97, more preferably from 0.98 to 1.005. If the spectral reflectance and the reflectance ratio are lower, it becomes difficult to obtain intended high-quality terephthalic acid by the high temperature post-oxidation of the slurry containing such terephthalic acid crystals as described above. On the contrary, to obtain terephthalic acid crystals having too high spectral reflectance and reflectance ratio is desirable in obtaining very high quality terephthalic acid, but production costs for such crystals will become extremely high, thus being not practical. It should be noted that in prior art processes of preparing terephthalic acid by high temperature post-oxidation, terephthalic acid crystals prior to high temperature post-oxidation have such a low reflectance ratio that the terephthalic acid obtained after the high temperature post-oxidation is not satisfactory with respect to the whiteness of polymer.

The slurry containing such terephthalic acid crystals as defined above is prepared under control of the first oxidation and, if necessary, low temperature post-oxidation. Various controlling factors are interrelated, typical of which are the following factors. These factors are appropriately combined so as to control the oxidation reaction as desired.

(1) The oxidation reaction temperature and pressures are increased.

(2) The amount of the catalyst is increased.

(3) The residence time for the first oxidation is prolonged.

(4) The concentration of oxygen in an oxidation reactor off-gas is raised.

Subsequently, the slurry containing the terephthalic acid crystals is subjected to high temperature post-oxidation. This operation is usually effected by charging the slurry under pressure into a high pressure zone by means of a pump and heating it to a predetermined temperature by a mono or multi-tube heat exchanger, thereby carrying out the post-oxidation. The high temperature oxidation may be effected according to any known processes including, for example, a process in which molecular oxygen is supplied to a heat exchanger and/or a high temperature post-oxidation reactor. The high temperature post-oxidation reactor may be of the same type as the first reactor.

The high temperature post-oxidation is carried out at a temperature of from 235° to 290° C., preferably from 240° to 280° C., and the pressure used should be at a level enough to maintain the reaction mixture as a liquid phase and is generally in the range of from 30 to 100 kg/cm$^2$. By the high temperature post-oxidation, part of the terephthalic acid crystals in the slurry is dissolved, so that the oxidation intermediate in the crystals is extracted in the mother liquor. The extracted oxidation intermediate is oxidized. Accordingly, if the temperature of the high temperature post-oxidation is too low, the extract of the oxidation intermediate in the terephthalic acid crystals does not proceed efficiently. On the contrary, too high a temperature is not only disadvantageous from the standpoint of energy, but also unfavorable in view of the possibility that colored impurities are produced.

The amount of the molecular oxygen to be supplied is usually from 0.03 to 0.3 moles, preferably from 0.01 to 0.1 mole, per mole of the terephthalic acid. In this connection, it is preferred that the concentration of oxygen in the oxidation reactor off-gas is substantially zero or at least not larger than 0.5% by volume. If the amount is too large, an amount of combustion of the acetic acid solvent increases because the system becomes high in temperature and an amount of a substance to be oxidized is small in amount. When the amount is too small, the effect of the high temperature post-oxidation is not produced adequately. The molecular oxygen used for this purpose may be air with or without dilution with an inert gas.

The reaction mixture obtained after completion of the high temperature post-oxidation is passed through a plurality of two to four-stage crystallization vessels wherein it is gradually decreased in temperature and pressure. Terephthalic acid crystals are separated from a final reaction mixture. In this crystallization step, when molecular oxygen is supplied to a zone (i.e. a crystallization vessel or transfer pipe) where the temperature of the mixture is of from 160° to 230° C., the quality of the terephthalic acid product is preferably further improved. The amount of the molecular oxygen is so controlled that the concentration of oxygen in the off-gas is in the range of from 0.5 to 8% by volume, preferably from 2 to 8% by volume. In that zone, the temperature of the reaction mixture is so low that even though a large amount of the molecular oxygen is supplied, the combustion of the acetic solvent rarely occurs.

The mixture obtained after completion of the crystallization treatment is usually subjected to solid-liquid separation, such as centrifugal separation, to collect crystals of terephthalic acid. If necessary, the terephthalic acid crystals are washed, for example, with water or acetic acid and dried to obtain a final product. On the other hand, the mother liquid is usually fed into a distillation column where the acetic acid is recovered by removal of the produced water, catalyst and side products. According to the process of the invention, the side products in the mother liquor and particularly impurities impeding the oxidation reaction are formed only in very small amounts. Accordingly, 10 to 80 wt % of the reaction mother liquor can be recycled to the first reactor.

Thus, according to the invention, terephthalic acid of high quality which is useful in preparing polyesters having a high degree of whiteness can be industrially, stably produced, thus being very advantageous from industrial and economical standpoint.

(EXAMPLES)

The present invention is more particularly described by way of examples, which should not be construed as limiting the present invention. Comparative examples are also shown. In these examples, parts are by weight.

EXAMPLES 1-4 AND COMPARATIVE EXAMPLES 1-2

Terephthalic acid was continuously prepared according to the flow chart shown in FIG. 1.

A first titanium autoclave 1 equipped with a reflux condenser, an agitator, a supply port for starting materials and a solvent, an air introducing port, and a reaction slurry withdrawal port was charged through a pipe 8 with 1 part of p-xylene, 4.5 parts of acetic acid containing 5% of water, and a mixture of cobalt acetate tetrahydrate in amounts indicated in Table 1, manganese acetate tetrahydrate used in amounts of 1.07 times by weight the cobalt acetate tetrahydrate, hydrobromic acid (47% aqueous solution) used in amounts of 1.51 times by weight the cobalt acetate tetrahydrate. The liquid phase oxidation reaction of p-xylene was effected under conditions of the residence time, temperature and pressure indicated in Table 1 while air used as an oxidative gas was supplied from a pipe 9 in such a way that the concentration of oxygen in the reactor off-gas was 6 vol. % and 1.5 parts of the refluxed liquor was withdrawn from a pipe 10 so as to control a concentration of water in the reactor or autoclave 1 at about 10%.

The mixture from the first reactor 1 was continuously fed into a second reactor 2 having similar equipments as the first reactor 1. In the second reactor 2, low temperature oxidation was effected while using a temperature lower by 10° C. than the temperature of the first reactor, a pressure lower by 3 kg/cm$^2$ than the pressure of the first reactor, and a residence time of 20 minutes and feeding air from a pipe 11 so that a concentration of oxygen in the off-gas was 4 vol. %.

The terephthalic acid crystals contained in the resultant slurry were subjected to measurement of spectral reflectance and reflectance ratio, with the results shown in Table 1. The spectral reflectance of the terephthalic acid crystals obtained in Example 1 at a wavelength of from 380 to 700 nm is shown in FIG. 2.

TABLE 1

|  | Cobalt Acetate (tetra-hydrate) (parts) | First Reaction Conditions | | | Terephthalic Acid | | |
| --- | --- | --- | --- | --- | --- | --- | --- |
|  |  | Residence Time (minutes) | Temperature (°C.) | Pressure (kg/cm$^2$) | Spectral Reflectance 500 nm (%) | Reflectance Ratio | |
|  |  |  |  |  |  | 400/500 | 450/500 |
| Ex. 1 | 0.0056 | 90 | 215 | 24 | 86.0 | 0.964 | 0.997 |
| 2 | 0.0056 | 80 | 205 | 19 | 84.7 | 0.932 | 0.981 |
| 3 | 0.0045 | 90 | 205 | 19 | 85.2 | 0.955 | 0.992 |

TABLE 1-continued

| | Cobalt Acetate (tetrahydrate) (parts) | First Reaction Conditions | | | Terephthalic Acid | | |
|---|---|---|---|---|---|---|---|
| | | Residence Time (minutes) | Temperature (°C.) | Pressure (kg/cm$^2$) | Spectral Reflectance 500 nm (%) | Reflectance Ratio | |
| | | | | | | 400/500 | 450/500 |
| 4 | 0.0045 | 120 | 215 | 24 | 85.4 | 0.976 | 0.997 |
| Com. Ex. | | | | | | | |
| 1 | 0.0033 | 70 | 195 | 15 | 85.0 | 0.874 | 0.958 |
| 2 | 0.0045 | 65 | 200 | 17 | 85.5 | 0.895 | 0.966 |

The mixture from the second reactor 2 was passed through a pipe 14 and its pressure was raised up to 55 kg/cm$^2$ by means of a pump 3. Thereafter, 0.07 parts of air was passed from a pipe 12 through a pipe 15 to the mixture, followed by charge into a mono-tube heater 4 wherein the temperature of the mixture was raised to 270° C. The mixture discharged from the heater 4 was fed through a pipe 16 into an agitated vessel of the same type as the first reactor, to which 0.03 parts of air was supplied from a pipe 17, followed by high temperature post oxidation under conditions of a temperature of 270° C., a pressure of 5 kg/cm$^2$ and a residence time of 30 minutes.

The mixture obtained after completion of the high temperature post-oxidation was subjected to three stage crystallization (crystallizers 6, 6', 6'') where it was gradually reduced to a normal pressure and cooled, followed by filtration with a centrifugal separator 7 to collect terephthalic acid crystals. The first crystallizer 6 was controlled under conditions of 200 and 11 kg/cm$^2$, to which air was charged from a pipe 18 so that a concentration of oxygen in the off-gas was 4 vol. %.

The thus collected terephthalic acid was subjected to measurement of spectral reflectance and reflectance ratio. Moreover, the acid was used to prepare a polyester, whose color tone (b value) was measured. The results are shown in Table 2. The spectral reflectance of the terephthalic acid crystals obtained in Example 1 at a wavelength of 380 to 700 nm are shown in FIG. 3.

TABLE 2

| | Spectral Reflectance (%) | Reflectance Ratio | | Color Tone of Polymer (b value) |
|---|---|---|---|---|
| | | 400/500 | 450/500 | |
| Example 1 | 87.1 | 0.988 | 1.001 | 1.0 |
| 2 | 86.9 | 0.968 | 0.991 | 1.5 |
| 3 | 84.5 | 0.977 | 0.996 | 1.2 |
| 4 | 87.2 | 0.993 | 1.001 | 0.8 |
| Com. Ex. 1 | 85.2 | 0.933 | 0.976 | 3.8 |
| 2 | 86.6 | 0.945 | 0.982 | 2.9 |

COMPARATIVE EXAMPLE 1

The general procedure of Comparative Example 1 was repeated except that the high temperature post-oxidation was effected at a temperature of 275° C. and a residence time of 45 minutes. The resultant terephthalic acid had a spectral reflectance of 86.7%, a reflectance ratio of 0.941 for 400/500 and 0.979 for 450/500, and a polymer color tone (b value) of 3.4.

Note (1) Measurement of the spectral reflectance

Sample terephthalic acid was charged into a quartz cell and subjected to measurement of spectral reflectance at 700 to 300 nm at intervals of 5 nm according to a white light illumination method using UV-365 Color Pack System Model 17 made by Shimadzu Co., Ltd., and a xenon lamp as a light source.

Note (2) Measurement of the polymer color tone (b value)

1.5 moles of terephthalic acid and 3.75 moles of, ethylene glycol were subjected to esterification reaction in the presence of 0.00028 moles of germanium dioxide and 0.00029 moles of phosphorus acid under conditions of 235° C. and 2.5 kg/cm$^2$G for 120 minutes, followed by reducing the pressure and increasing the temperature in 45 minutes to effect the polymerization under conditions of 280° C. and 1 mmHg for 120 minutes.

The chips of the resultant polymer were filled in a quartz cell and subjected to measurement of the b value using a differential colorimeter (TC-55D, available from Tokyo Denshoku K.K.). The b value means a yellowish color for "+" and a bluish color for "−" and a smaller b value is better for the polymer color tone.

Figure 1:
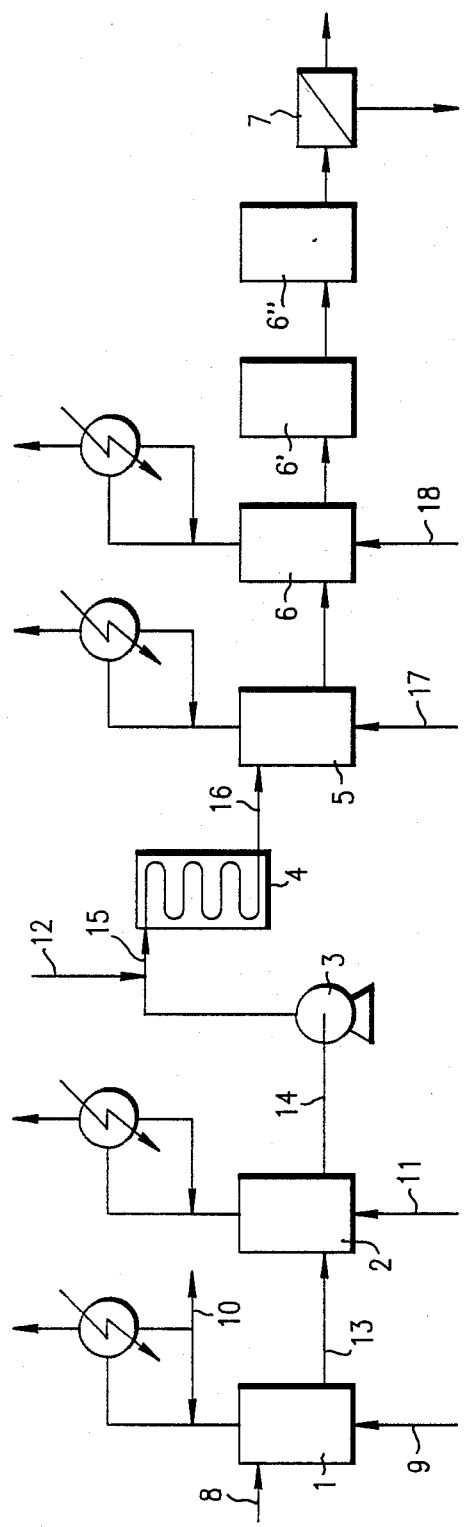
FIG. 1 is a flow chart showing a reactor used in the examples of the present invention.
Figure 2:
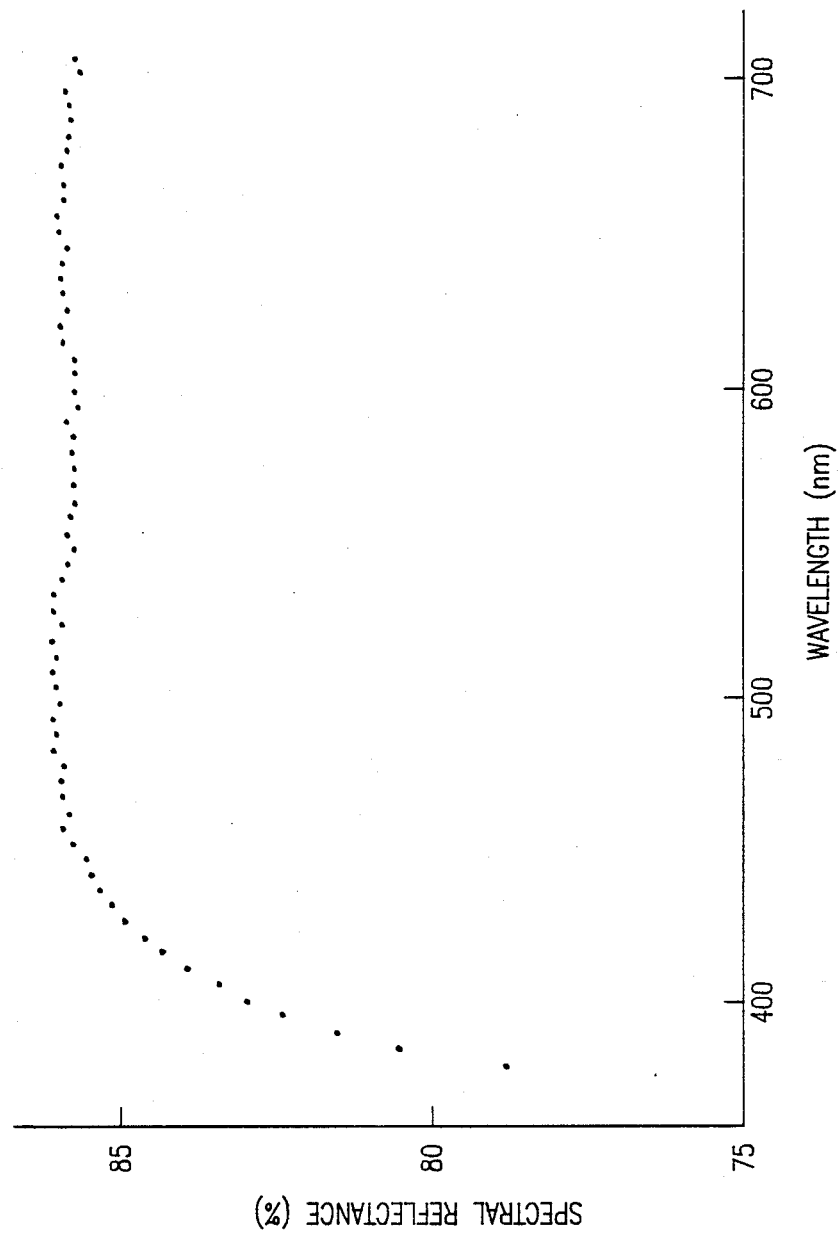
FIG. 2 is a graph showing a spectral reflectance of terephthalic acid crystals in a slurry obtained in Example 1 but prior to high temperature post-oxidation.
Figure 3:
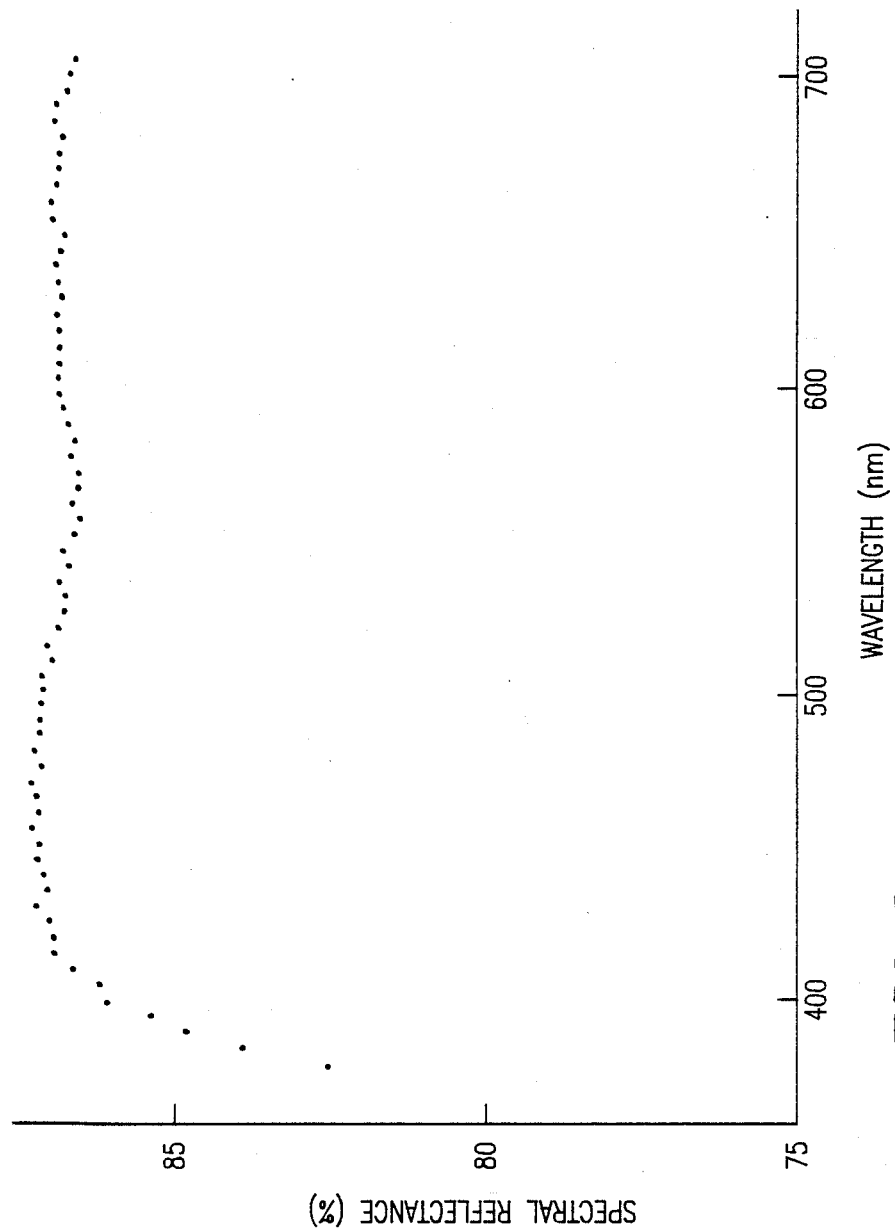
FIG. 3 is a graph showing a spectral reflectance of the terephthalic acid crystals collected in Example 1.

What is claimed is:

1. A process for preparing terephthalic acid of high quality which comprises:

oxidizing p-xylene with molecular oxygen in an acetic acid solvent in the presence of a catalyst comprised of at least one heavy metal and bromine at a temperature of from 180° to 230° C. to convert at least 95 wt % of the p-xylene into terephthalic acid and, optionally, subjecting the resultant reaction mixture to low temperature post-oxidation with molecular oxygen at temperatures lower than the temperature of the first oxidation reaction, thereby obtaining a slurry containing terephthalic acid particles whose spectral reflectance defined below is not less than 70% and whose reflectance ratio (400/500) defined below is not less than 0.92;

subjecting the slurry to high temperature post-oxidation with molecular oxygen at a temperature of from 235° to 290° C. and then to crystallization; and collecting the resultant terephthalic acid from the reaction mixture.

2. A process according to claim 1, wherein the terephthalic acid particles in the slurry which is subjected to the high temperature post-oxidation has a reflectance ratio (450/500) of not less than 0.97.

3. A process according to claim 1, wherein the terephthalic acid particles in the slurry which is subjected to the high temperature post-oxidation has a spectral reflectance of not less than 80% and a reflectance ratio (400/500) of from 0.93 to 0.98.

4. A process according to claim 3, wherein the collected terephthalic acid has a spectral reflectance of not less than 80% and a reflectance ratio (400/500) of from 0.965 to 1.005.

5. A process according to claim 1, wherein said catalyst is a ternary catalyst consisting essentially of cobalt, manganese and bromine.

6. A process according to claim 1, wherein the pressure of the first oxidation reaction ranges from 10 to 30 kg/cm$^2$.

7. A process according to claim 1, wherein the time of the first oxidation reaction ranges from 40 to 150 minutes.

8. A process according to claim 1, wherein a concentration of oxygen in an off-gas from the first oxidation reaction is in the range of from 1.5 to 8% by volume.

9. A process according to claim 1, wherein a concentration of water in a liquid phase of the first oxidation reaction is in the range of from 5 to 15 wt %.

10. A process according to claim 1, wherein a feed to the molecular oxygen in the first oxidation reaction is from 3 to 100 times by mole a feed of the p-xylene.

11. A process according to claim 1, wherein the low temperature post-oxidation is effected after the first oxidation reaction.

12. A process according to claim 1 or 11, wherein the temperature of the low temperature post-oxidation is lower by 2° to 30° C. than the temperature of the first oxidation reaction.

13. A process according to claim 1 or 11, wherein the reaction time of the low temperature post-oxidation is in the range of from 5 to 90 minutes.

14. A process according to claim 1 or 11, wherein a feed of molecular oxygen used in the low temperature post-oxidation is 1/10 to 1/1000 of the feed in the first oxidation reaction.

15. A process according to claim 1, wherein the temperature of the high temperature post-oxidation is in the range of from 240° to 280° C.

16. A process according to claim 1, wherein the pressure of the high temperature post-oxidation is in the range of from 30 to 100 kg/cm$^2$.

17. A process according to claim 1, wherein a concentration of oxygen in an off-gas from the high temperature post-oxidation is not larger than 0.5% by volume.

18. A process according to claim 1 or 17, wherein a feed of molecular oxygen used in the high temperature post-oxidation reaction is in the range of from 0.003 to 0.3 times by mole the amount of terephthalic acid in the slurry.

19. A process according to claim 1, wherein during the crystallization, molecular oxygen is fed into the slurry in a zone where the temperature is from 160° to 230° C. in such an amount that a concentration of the oxygen in the off-gas is from 2 to 8% by volume.

* * * * *